United States Patent
Chen et al.

(10) Patent No.: US 9,518,934 B2
(45) Date of Patent: Dec. 13, 2016

(54) WAFER DEFECT DISCOVERY

(71) Applicant: KLA-Tencor Corporation, Milpitas, CA (US)

(72) Inventors: Hong Chen, San Ramon, CA (US); Kenong Wu, Davis, CA (US); Martin Plihal, Pleasanton, CA (US); Vidur Pandita, UttarPradesh (IN); Ravikumar Sanapala, San Jose, CA (US); Vivek Bhagat, Fremont, CA (US); Rahul Lakhawat, Chennai (IN); Oksen Baris, San Francisco, CA (US); Rajesh Ramachandran, Fremont, CA (US); Naoshin Haque, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/931,226

(22) Filed: Nov. 3, 2015

(65) Prior Publication Data
US 2016/0123898 A1    May 5, 2016

Related U.S. Application Data

(60) Provisional application No. 62/075,002, filed on Nov. 4, 2014.

(51) Int. Cl.
*G01N 21/00* (2006.01)
*G01N 21/95* (2006.01)
(Continued)

(52) U.S. Cl.
CPC ...... *G01N 21/9501* (2013.01); *G01N 21/8851* (2013.01); *G03F 7/70625* (2013.01);
(Continued)

(58) Field of Classification Search
CPC .............................. G01N 21/00; G01N 21/956
(Continued)

(56) References Cited

U.S. PATENT DOCUMENTS 5,903,342 A * 5/1999 Yatsugake .............. G01N 21/94
                                                        250/559.41
5,999,003 A   12/1999 Steffan et al.
(Continued)

OTHER PUBLICATIONS

International Search Report and Written Opinion for PCT/US2015/059085 mailed Jan. 29, 2016.

*Primary Examiner* — Roy M Punnoose
(74) *Attorney, Agent, or Firm* — Ann Marie Mewherter (57) ABSTRACT

Systems and methods for discovering defects on a wafer are provided. One method includes detecting defects on a wafer by applying a threshold to output generated by a detector in a first scan of the wafer and determining values for features of the detected defects. The method also includes automatically ranking the features, identifying feature cut-lines to group the defect into bins, and, for each of the bins, determining one or more parameters that if applied to the values for the features of the defects in each of the bins will result in a predetermined number of the defects in each of the bins. The method also includes applying the one or more determined parameters to the output generated by the detector in a second scan of the wafer to generate a defect population that has a predetermined defect count and is diversified in the values for the features.

20 Claims, 6 Drawing Sheets

(51) Int. Cl.
*G01N 21/88* (2006.01)
*G03F 7/20* (2006.01)

(52) U.S. Cl.
CPC ............... *G01N 2021/8854* (2013.01); *G01N 2021/8883* (2013.01)

(58) Field of Classification Search
USPC .................................................. 356/237.5
See application file for complete search history.

(56) References Cited

U.S. PATENT DOCUMENTS

| | | |
|---|---|---|
| 8,664,594 B1 | 3/2014 | Jiang et al. |
| 8,692,204 B2 | 4/2014 | Kojima et al. |
| 8,698,093 B1 | 4/2014 | Gubbens et al. |
| 8,716,662 B1 | 5/2014 | MacDonald et al. |
| 2006/0124874 A1* | 6/2006 | Uto .................... G01N 21/9501 250/559.45 |
| 2008/0167829 A1 | 7/2008 | Park et al. |
| 2009/0299681 A1 | 12/2009 | Chen et al. |
| 2013/0202189 A1 | 8/2013 | Shibuya et al. |
| 2014/0016125 A1* | 1/2014 | Sullivan ............. G01N 21/9501 356/237.5 |
| 2014/0050389 A1 | 2/2014 | Mahadevan et al. |

\* cited by examiner

WAFER DEFECT DISCOVERY

BACKGROUND OF THE INVENTION

1. Field of the Invention

The present invention generally relates to systems and methods for discovering defects on a wafer, which are particularly useful for setting up a wafer inspection process.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

Many different types of inspection systems have adjustable output acquisition (e.g., data, signal, and/or image acquisition) and sensitivity (or defect detection) parameters such that different parameters can be used to detect different defects or avoid sources of unwanted (nuisance) events. Although an inspection system that has adjustable output acquisition and sensitivity parameters provides significant advantages to a semiconductor, device manufacturer, these inspection systems are essentially useless if the incorrect output acquisition and sensitivity parameters are used for an inspection process. In addition, since the defects, process conditions, and noise on wafers may vary dramatically (and since the characteristics of the wafers themselves may vary dramatically), the best output acquisition and sensitivity parameters for detecting defects on a particular wafer may be difficult, if not impossible, to predict. Therefore, although using the correct output acquisition and sensitivity parameters will have a dramatic effect on the results of inspection, it is conceivable that many inspection processes are currently being performed with incorrect or non-optimized output acquisition and sensitivity parameters.

An optimal inspection recipe for a semiconductor layer should detect as many defects of interest (DOIs) as possible while maintaining a substantially low nuisance rate. Optimizing an inspection recipe generally involves tuning the parameters used in the recipe until the optimal result is achieved. The set of parameters to be tuned thus depends on the detection algorithm used.

One best known method for recipe optimization is to run a substantially "hot" inspection thereby increasing the likelihood of detecting DOI but at the expense of substantially high nuisance rates. The user then takes this hot lot and the wafer to a scanning electron microscope (SEM) for review. The user reviews the defects using the SEM and classifies the defects as real, nuisance, or DOI. Once enough of each type of defect is classified, the user attempts to set the correct defect detection parameter values in order to create a recipe that will detect enough of the DOI and have as few as possible of the nuisance defects detected. The more defects that are classified, the better the recipe can be. The user may then re-inspect the wafer using the new recipe and use the SEM to review the defects detected on the wafer using the new recipe. In this manner, re-inspection and defect review may be performed in an iterative manner until the user determines that satisfactory defect detection can be achieved by the recipe based on defect review results.

One problem with such methods is that it takes significant time to SEM review a single defect. In addition, the need for multiple trips between the inspection system and the SEM adds significant time to the recipe setup. The user would ideally like to review the smallest number of defects possible that would still produce an accurate recipe and be able to do this in one trip to the SEM.

Accordingly, it would be advantageous to develop systems and methods for discovering defects on a wafer that do not have one or more of the disadvantages described above.

SUMMARY OF THE INVENTION

The following description of various embodiments is not to be construed in any way as limiting the subject matter of the appended claims.

One embodiment relates to a system configured to discover defects on a wafer. The system includes an inspection subsystem comprising at least an energy source and a detector. The energy source is configured to generate energy that is directed to and scanned over a wafer. The detector is configured to detect energy from the wafer and to generate output responsive to the detected energy. The system also includes a computer subsystem configured for detecting defects on the wafer by applying a threshold to the output generated by the detector in a first scan of the wafer. The computer subsystem is also configured for determining values for features of the detected defects. In addition, the computer subsystem is configured for, based on the values for the features, automatically ranking the features and identifying feature cut-lines to group the defects into bins. The computer subsystem is further configured for, for each of the bins, determining one or more parameters that if applied to the values for the features of the defects in each of the bins will result in a predetermined number of the defects in each of the bins. The computer subsystem is also configured for applying the one or more determined parameters to the output generated by the detector in a second scan of the wafer to generate a defect population. The defect population has a predetermined defect count and is diversified in the values for the features. The system may be further configured as described herein.

Another embodiment relates to a computer-implemented method for discovering defects on a wafer. The method includes the detecting, determining values, automatically ranking, identifying, determining one or more parameters, and applying performed by the computer subsystem described above. Each of the steps of the method may be further performed as described herein. In addition, the method may include any other step(s) of any other method(s) described herein. Furthermore, the method may be performed by any of the systems described herein.

Another embodiment relates to a non-transitory computer-readable medium storing program instructions executable on a computer system for performing a computer-implemented method for discovering defects on a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

Figure 1:
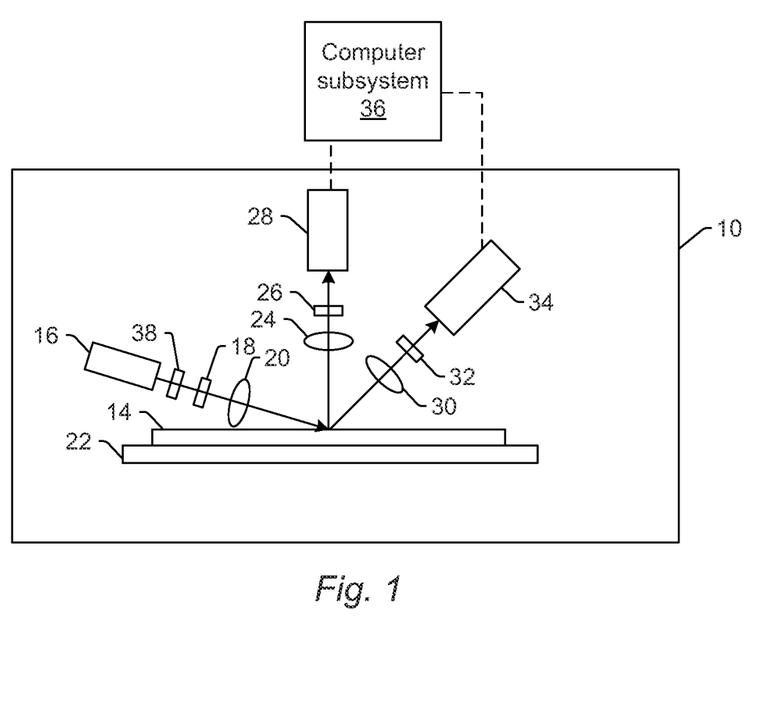
FIGS. 1-1a are schematic diagrams illustrating side views of embodiments of a system configured to discover defects on a wafer.

The embodiments described herein are configured to perform a one step tuning scan (OSTS) for wafer defect discovery. One embodiment relates to a system configured to discover defects on a wafer, and one such system is shown in FIG. 1. The system includes an inspection subsystem that includes at least an energy source and a detector. The energy source is configured to generate energy that is directed to and scanned over a wafer. The detector is configured to detect energy from the wafer and to generate output responsive to the detected energy.

In one embodiment, the energy source includes a light source, the energy that is directed to and scanned over the wafer includes light, and the detected energy includes detected light. For example, in the embodiment of the system shown in FIG. 1, inspection subsystem 10 includes an illumination subsystem configured to direct light to wafer 14. The illumination subsystem includes at least one light source. For example, as shown in FIG. 1, the illumination subsystem includes light source 16. In one embodiment, the illumination subsystem is configured to direct the light to the wafer at one or more angles of incidence, which may include one or more oblique angles and/or one or more normal angles. For example, as shown in FIG. 1, light from source 16 is directed through optical element 18 and then lens 20 to wafer 14 at an oblique angle of incidence. The oblique angle of incidence may include any suitable oblique angle of incidence, which may vary depending on, for instance, characteristics of the wafer and the defects to be detected on the wafer.

The illumination subsystem may be configured to direct the light to the wafer at different angles of incidence at different times. For example, the inspection subsystem may be configured to alter one or more characteristics of one or more elements of the illumination subsystem such that the light can be directed to the wafer at an angle of incidence that is different than that shown in FIG. 1. In one such example, the inspection subsystem may be configured to move light source 16, optical element 18, and lens 20 such that the light is directed to the wafer at a different oblique angle of incidence or a normal (or near normal) angle of incidence.

In some instances, the illumination subsystem may be configured to direct light to the wafer at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the wafer at the same time as the other light, one or more characteristics (e.g., wavelength, polarization, etc.) of the light directed to the wafer at different angles of incidence may be different such that light resulting from illumination of the wafer at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the wafer. Multiple illumination channels may be configured to direct light to the wafer at the same time or at different times (e.g., when different illumination channels are used to sequentially illuminate the wafer). In another instance, the same illumination channel may be configured to direct light to the wafer with different characteristics at different times. For example in some instances, optical element 18 may be configured as a spectral filter and the properties of the spectral filter can be changed in a variety of different ways (e.g., by changing the spectral filter) such that different wavelengths of light can be directed to the wafer at different times. The illumination subsystem may have any other suitable configuration known in the art for directing the light having different or the same characteristics to the wafer at different or the same angles of incidence sequentially or simultaneously.

In one embodiment, light source 16 may include a broadband plasma (BBP) light source. In this manner, the light generated by the light source and directed to the wafer may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths of wavebands.

Light from optical element 18 may be focused onto wafer 14 by lens 20. Although lens 20 is shown in FIG. 1 as a single refractive optical element, it is to be understood that, in practice, lens 20 may include a number of refractive and/or reflective optical elements that in combination focus the light from the optical element to the wafer. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the inspection subsystem may be configured to alter one or more of the elements of the illumination subsystem based on the type of illumination to be used for inspection.

The inspection subsystem may also include a scanning subsystem configure to cause the light to be scanned over the wafer. For example, the inspection subsystem may include stage 22 on which wafer 14 is disposed during inspection. The scanning subsystem may include any suitable mechanical and/or robotic assembly (that includes stage 22) that can be configured to move the wafer such that the light can be scanned over the wafer. In addition, or alternatively, the inspection subsystem may be configured such that one or more optical elements of the inspection subsystem perform some scanning of the light over the wafer. The light may be scanned over the wafer in an suitable fashion such as in a serpentine-like path or in a spiral path.

The inspection subsystem further includes one or more detection channels. At least one of the one or more detection channels includes a detector configured to detect light from the wafer due to illumination of the wafer by the inspection subsystem and to generate output responsive to the detected light. For example, the inspection subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, both detection channels are configured to detect scattered light, and the detection channels are configured to detect light that is scattered at different angles from the wafer. However, one or more of the detection channels may be configured to detect another type of light from the wafer (e.g., reflected light).

As further shown in FIG. 1, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 30, element 32, and detector 34 may be configured to collect and detect light that is scattered out of the plane of incidence. Therefore, such a detection channel may be commonly referred to as a. "side" channel, and such a side channel may be centered in a plane that is substantially perpendicular to the plane of incidence.

Although FIG. 1 shows an embodiment of the inspection subsystem that includes two detection channels, the inspection subsystem may include a different number of detection channels (e.g., only one detection channel or two or more detection channels). In one such instance, the detection channel formed by collector 30, element 32, and detector 34 may form one side channel as described above, and the inspection subsystem may include an additional detection channel (not shown) formed as another side channel that is positioned on the opposite side of the plane of incidence. Therefore, the inspection subsystem may include the detection channel that includes collector 24, element 26, and detector 28 and that is centered in the plane of incidence and configured to collect and detect light at scattering angle(s) that are at or close to normal to the wafer surface. This detection channel may therefore be commonly referred to as a "top" channel, and the inspection subsystem may also include two or more side channels configured as described above. As such, the inspection subsystem may include at least three channels (i.e., one top channel and two side channels), and each of the at least three channels has its own collector, each of which is configured to collect light at different scattering angles than each of the other collectors.

As described further above, each of the detection channels included in the inspection subsystem may be configured to detect scattered light. Therefore, the inspection subsystem shown in FIG. 1 may be configured for dark field (DF) inspection of wafers. However, the inspection subsystem may also or alternatively include detection channel(s) that are configured for bright field (BF) inspection of wafers. In other words, the inspection subsystem may include at least one detection channel that is configured to detect light spectrally reflected from the wafer. Therefore, the inspection subsystems described herein may be configured for only DF, only BF, or both DF and BF inspection. Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the inspection subsystem may be signals or data, but not image signals or image data. In such instances, a computer subsystem such as computer subsystem 36 of the system may be configured to generate images of the wafer from the non-imaging output of the detectors. However, in other instances, the detectors may be configured as imaging detectors that are configured to generate imaging signals or image data. Therefore, the system may be configured to generate images in a number of ways.

It is noted that FIG. 1 is provided herein to generally illustrate a configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection subsystem (e.g., by adding functionality described herein to an existing inspection system) such as the 29xx/28xx series of tools that are commercially available front KLA-Tencor, Milpitas, Calif. For some such systems, the methods described herein may be provided as optional functionality of the inspection system (e.g., in addition to other functionality of the inspection system). Alternatively, the inspection subsystem described herein may be designed "from scratch" to provide a completely new inspection system.

Computer subsystem 36 of the system may be coupled to the detectors of the inspection subsystem in any suitable manner via one or more transmission media, which may include "wired" and/or "wireless" transmission media) such that the computer subsystem can receive the output generated by the detectors during scanning of the wafer. Computer subsystem 36 may be configured to perform a number functions using the output of the detectors. For instance, the computer subsystem is configured to detect defects on the wafer by applying a threshold to the output generated by the detector in a first scan of the wafer. The threshold may be included in any suitable defect detection algorithm and/or method known in the art. Any output having values above the threshold may be identified as a defect while any output having values below the threshold may not be identified as a defect.

In one embodiment, the threshold is at a noise floor of the output. The noise floor is defined based on the user-specified pixel density in a histogram of a difference image. The threshold offset indicates how far a threshold is from the noise floor. For example, the threshold at the noise floor means a threshold offset of 0. In another embodiment, the threshold is automatically selected by the computer subsystem. In this manner, the threshold may be an auto-selected threshold. The computer subsystem of the system may be further configured as described herein.

The computer subsystem of the system (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

Although the system is described above as being an optical or light-based inspection system, the inspection system may be an electron beam-based system. For example, in one embodiment, the energy source includes an electron beam source, the energy that is directed to and scanned over the wafer includes electrons, and the detected energy includes detected electrons. In one such embodiment shown in FIG. 1a, the system includes an inspection subsystem configured as electron column 122 coupled to computer subsystem 124.

Figure 1A:
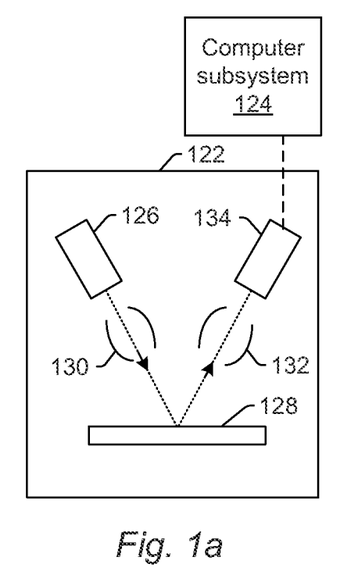

As also shown in FIG. 1a, the electron column includes electron beam source 126 configured to generate electrons that are focused to wafer 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the wafer (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 1a as being configured such that the electrons are directed to the wafer at an oblique angle of incidence and are scattered from the wafer at another oblique angle, it is to be understood that the electron beam may be directed to and scattered from the wafer at any suitable angles. In addition, the electron beam-based inspection system may be configured to use multiple modes to generate images of the wafer as described further herein (e.g., with different illumination angles, collection angles, etc.). The multiple modes of the electron beam-based inspection subsystem may be different in any image generation parameters of the inspection subsystem.

Computer subsystem 124 may be coupled to detector 134 as described above. The detector may detect electrons returned from the surface of the wafer thereby forming electron beam images of the wafer. The electron beam images may include any suitable electron beam images. Computer subsystem 124 may be configured to detect defects on the wafer as described further herein using output generated by detector 134. Computer subsystem 124 may be configured to perform any additional step(s) described herein. A system that includes the inspection subsystem shown in FIG. 1a may be further configured as described herein.

It is noted that FIG. 1a is provided herein to generally illustrate a configuration of an electron beam-based inspection subsystem that may be included in the embodiments described herein. As with the optical inspection subsystem described above, the electron beam-based inspection subsystem configuration described herein may be altered to optimize the performance of the inspection subsystem as is normally performed when designing a commercial inspection system. In addition, the systems described herein may be implemented using an existing inspection subsystem by adding functionality described herein to an existing inspection subsystem) such as the eSxxx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

The computer subsystem (e.g., computer subsystem 36 or computer subsystem 124) is also configured for determining values for features of the detected defects. For example, during the first scan described above, the computer subsystem may compute and collect various features for each defect detected. In particular, the computer subsystem may use output and/or information about the output generated for the locations on the wafer at which the defects were detected to determine values for features of the detected defects. The values for the features may or may not be quantitative values. For example, the values for the features may include values for gray level or intensity. However, the values for the features may also include qualitative values such as die type in which the defect was detected, region type in which the defect was detected, polarity indicating whether the defect is brighter than its background, and the like. The values for any of such features may be determined in any suitable manner. In addition, the features of the defects may include any other defect features described herein or known in the art.

The computer subsystem is also configured for based on the values for the features (e.g., the collected feature information from the first scan), automatically ranking the features (i.e., defect features and identifying feature cut-lines to group the defects into bins (or sub-groups). For example, various defect features may be computed and then ranked automatically. Top-ranked features may be used to group defects into different subgroups (bins). In this manner, multiple levels of defect feature nodes can be used to group defects. Each node can select different features based on the ranking. In this manner, the results of automatically ranking the features and identifying the feature cut-lines may produce a defect classification model, method, or algorithm such as a defect classification decision tree.

In one example of selecting the diversification nodes and cut-lines for each node, if a user selects die type, region, and polarity, these may be top nodes. Below polarity, user-specified layers of nodes (for instance, 1, 2, or 3) can be selected from features that have been saved from the first scan. Each node and cut-lines per node can be selected using an approach similar to that used in power-assisted node and cut-line selection in the IMPACT product that is commercially available from KLA-Tencor, Milpitas, Calif. The layers of nodes and maximum cut-lines can be specified in the recipe.

The computer subsystem is also configured for, for each of the bins, determining one or more parameters that if applied to the values for the features of the defects in each of the bins will result in a predetermined number of the defects in each of the bins. In one embodiment, the one or more determined parameters include one or more thresholds. For example, different threshold parameters may be applied in each subgroup (bin) divided by some of the above-defect features to achieve the desired total defect count. In this manner, for each subgroup, a desired number of defects can be achieved with one or more particular threshold parameters.

In some embodiments, the one or more determined parameters include one or more parameters for nuisance filtering. For example, a nuisance filter used in the embodiments described herein may be configurable so that users can adjust the diversification criteria to specific layers/devices/etc. In addition, the embodiments described herein may be configured for automatically collecting a user-specified amount of defects for nuisance filter setup without manual user recipe setup.

Figure 2:
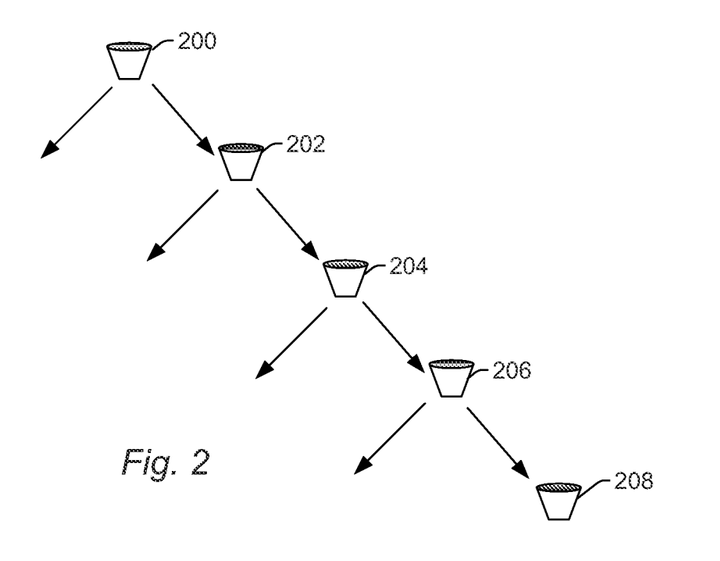
FIG. 2 is a schematic diagram illustrating one embodiment of results of automatically ranking features of detected defects.

FIG. 2 illustrates one embodiment of how to generate a diversified defect population. For example, in the embodiment of FIG. 2, bin 200 may be for one die type and may contain, in just one hypothetical example, 125,000 defects. The defects in bin 200 may then be separated based on region in the die type into bin 202 and one or more other bins (not shown). The number of defects in bin 202 may be, in the hypothetical example described above, 100,000 defects. The defects in bin 202 may then be separated based on polarity into bin 204 and one or more other bins (not shown). The number of defects in bin 204 may be, in the hypothetical example described above, 25,000 defects. The defects in bin 204 may then be separated based on a parameter of a defect detection algorithm such as median gray level of the multi-die auto-thresholding (MDAT) algorithm that is used for defect detection by some inspection tools that are commercially available from KLA-Tencor into bin 206 and one or more other bins (not shown). The number of defects in bin 206 may be, in the hypothetical example described above, 12,500 defects. The defects in bin 206 may then be separated based on another parameter of the defect detection algorithm such as threshold offset into bin 208 and one or more other bins (not shown). The defect detection parameters that are used in the last layers may be selected to achieve the targeted number of defects.

In another embodiment, the predetermined number of the defects is selected by a user. For example, the embodiments described herein are configured for automatically collecting a user-specified amount of defects for one step recipe tuning without manual user recipe setup. In an additional embodiment, the predetermined number of the defects is different for at least two of the bins. In some such embodiments, a user can specify, the percentage defects from primary and secondary dies, specify percentage defects from regions, and even percentage polarity per region. If one particular node does not have enough defects, the remaining defect quota can be redistributed to other nodes at the same levels to generate user-desired total defect counts. For instance, if there are not enough defects from one region, the extra defect quota can be redistributed to other regions.

The computer subsystem is further configured for applying the one or more determined parameters to the output generated by the detector in a second scan of the wafer to generate a defect population. The discovery OSTS described herein may therefore include two scans. In addition, as described above, between the first and second OSTS scans, the computer subsystem identifies recipe parameters and nuisance filter to collect a targeted number of diversified defects. The second scan may be performed in any suitable manner. The defect population may be generated by the second scan as described further herein, e.g., applying the one or more determined parameters to output of one or more detectors of the inspection subsystem generated during the second scan.

The defect population has a predetermined defect count and is diversified in the values for the features. For example, the goal of the embodiments described herein may be to generate a lot of results with a desired total defect count and a diversified defect population to help users quickly discover defects of interest (DOIs). In this manner, in the second scan, recipe parameters and nuisance filter identified after the first scan are applied in the second scan to achieve the desired defect count with a diversified defect population. Diversification is achieved by collecting defects distributed in a multi-dimensional space defined with different defect features. As such, the embodiments described herein may be configured for defect diversification and nuisance filter "training" in hot scan creation.

In one embodiment, the computer subsystem is further configured for performing the detecting, determining the values, automatically ranking, identifying, determining the one or more parameters, and applying automatically and without manual recipe setup. For example, the embodiments described herein can be used for automatically detecting diversified defects on semiconductor wafers without manual user recipe setup.

As described above, the embodiments may include one initial scan. However, the embodiments may perform subsequent runs of the initial scan for iterative tuning. The iterations could include running a scan with 0 threshold offset the first time. After each iteration, the computer subsystem may be configured for finding the nuisance filter that achieves the desired defect count with the desired diversification and raising the detection thresholds to a level that does not remove significant numbers of defects with the nuisance filter attached. If the detection offsets are raised, they may be applied to the recipe and a scan may be performed with the new thresholds. This process may be repeated until the stopping criteria is reached. In this manner, the embodiments described herein may be configured for simultaneous iterative tuning of detection thresholds and nuisance filters.

Some methods and systems for OSTS have been developed but have a number of disadvantages. For example, some currently used OSTS methods collect defects with an aggressive defect detection threshold and automatically adjust thresholds in sub-groups to achieve a desired defect count. The currently used methods also work with much fewer diversification dimensions and cannot collect a diversified defect population based on different defect features. In addition, the currently used methods are not flexible by working with a fixed diversification scheme. The currently used methods further are weak in nuisance suppression, work only for one particular detection algorithm, and are highly dependent on wafer defectivity and not on defect background.

The embodiments described herein have a number of advantages over such currently used methods. For example, it is a common practice on BBP tools today to use nuisance filters to achieve the desired sensitivity and nuisance rate in production inspections. These nuisance filters employ the very same strategy of diversification followed by tuning. In order to tune such inspection recipes, good training lot results and efficient sampling schemes are needed to produce good training data for all of the leaf nodes of the nuisance filters. The embodiments described herein will make it possible to generate quick and reliable good training lot results with sufficient defect counts in all nodes of the nuisance filters to be tuned. The embodiments also close the loop that will enable a unified recipe tuning approach that takes into account the necessary defect diversification throughout the tuning process, i.e., (a) data collection (hot scans), (b) sampling (for scanning electron microscope (SEM) review to obtain ground truth), and (c) nuisance filter tuning based on the classified defects. The embodiments described herein also improve the time to results. For example, in the old approach, the user has to invest a lot of time in running and tuning a scan (sometimes more than once) to achieve the desired results. In contrast, the embodiments described herein reduce that time significantly. In addition, the currently used methods require a certain level of application engineer skill set to run a good scan especially for logic regions. In contrast, the embodiments described herein will be more efficient and remove a lot of manual work from the application engineer side.

Additional embodiments described herein are configured for multi-mode adaptive defect discovery. For example, in one embodiment, the inspection subsystem is configured to scan the wafer with different optics modes. In one such example, defect discovery using a BBP optical inspector employs multiple wafer scans with a diverse set of optics modes to maximize the probability of detecting all defect types on a wafer. A "mode" can be generally defined as a set of parameters that can be used collectively to generate output for a wafer. Therefore, different modes will have at least one different parameter such as different illumination conditions, different collection/detection conditions, etc. In this manner, each mode can be thought of as a different "perspective" of the wafer. Some modes can be used in the same scan of a wafer. However, some modes can only be used in different scans of a wafer. Therefore, the scanning of the wafer with different modes described herein may include one or more scans. The number of modes being used for discovery has been steadily increasing, and currently the best known mode (BKM) is 27 modes. The embodiments described herein provide a new method for processing this rich information in a much more efficient way that is very likely to produce better and faster discovery results.

Some currently used methods for discovery of defect types on a wafer include identifying a set of diverse optics modes on the BBP tool that basically cover the entire spectrum of optical conditions. (The current BKM is to use 27 modes.) In addition, the currently used methods include, after scanning the wafer with each mode and producing a hot inspection for all of them, performing commonality analysis to find which defects were found in which modes. The capture rate for each unique defect may be calculated. (Capture rate equals fraction of modes that detected the defect.) Duplicate instances of detected defects are removed, and the defect from the first mode where it was detected is kept. The results generated using each mode are then processed independently using discovery (diversity) sampling to find a diverse set of defects in each mode. This step also includes the capability to identify defects in the mode that is being currently processed, which have already been sampled in previous modes, and then diversifying with respect to those defects as well.

Figure 3:
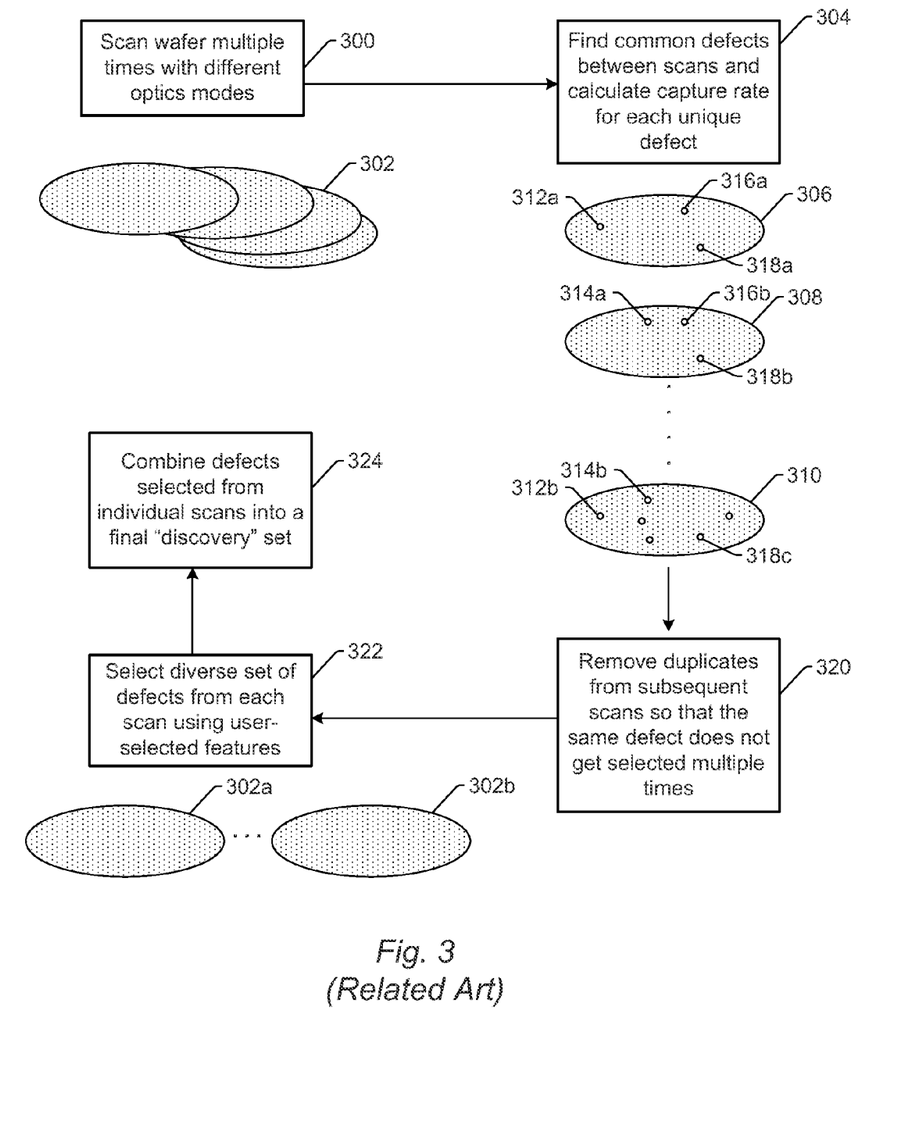
FIG. 3 is a flow chart illustrating one currently used method for discovering defects on a wafer.

FIG. 3 shows this method schematically. For example, as shown in step 300, the method may include scanning a wafer multiple times with different optics modes. Each mode may therefore generate different inspection results 302, one for each mode. As shown in step 304, the method may include finding common defects between scans (modes) and calculating the capture rate for each unique defect. For instance, for inspection results 306, 308, and 310 shown in FIG. 3 generated with different modes, a number of defects may be common to two or more of the results. In particular, defects 312a and 312b are common to inspection results 306 and 310, defects 314a and 314b are common to inspection results 308 and 310, defects 316a and 316b are common to inspection results 306 and 308, and defects 318a, 318b, and 318c are common to inspection results 306, 308, and 310.

As shown in step 320, the method may include removing duplicates from subsequent scans (modes) so that the same defect does not get selected multiple times. In addition, as shown in step 322, the method may include selecting a diverse set of defects from each scan (mode) using user-selected features. For example, the method may include selecting a diverse set of defects from inspection results 302a generated with one scan performed with one mode and selecting a diverse set of defects from inspection results 302b generated with another scan performed with another mode. As further shown in step 324, the method may include combining defects selected from individual scans (modes) into a final "discovery" set.

The currently used methods such as that described above have two significant disadvantages with respect to the embodiments described herein. First, users must select the set of defect attributes that they believe will give them the best and most relevant diversification. Even though this knowledge is to some extent available, there could always be a better set of attributes for a given wafer that cannot be identified today. In addition, the way the multi-mode information is used is extremely clumsy. Essentially, each mode is processed independently of one another with the exception of eliminating the duplicates, using defect capture rate as mode-related information and possibly leveraging the diversification mechanism across modes by identifying which defects were already sampled in other modes. Furthermore, the wealth of information encoded in the multiple sets of properties each defect has from the multiple modes is simply not used today. (Defects tend to have different optical appearances in different modes, and these differences can be exploited to find unique defect types.)

The embodiments described further herein may employ a machine learning algorithm that builds a defect classification model from a training set of labeled data points. The model generates (a) defect classification and (b) classification confidence for the defects that it did not train on. This information can then be used to search for defect types that are not known to the model.

In one such embodiment, the computer subsystem is configured for detecting other defects based on the output generated with the different modes, determining values for features of the other defects using the output generated with the different modes, and performing defect discovery based on a combination of all of the values for all of the features determined for all of the defects. For example, the embodiments may include scanning a wafer one or more times with different modes. Output generated by detector(s) of the inspection system for each of the different modes may be used as described further herein to defect defects on the wafer. In addition, the method may include determining values for features of the defects detected by each of the different modes as described herein. All of the values for all of the features for all of the defects may then be used collectively as described further herein to perform defect discover.

In another such embodiment, the computer subsystem is configured for detecting other defects based on the output generated with the different modes, comparing the other defects to identify the different modes with which each of the other defects was detected, determining a set of features for each of the other defects, the set of features is determined based on the output generated with the different modes, and searching the other defects for different types of defects based on the set of features. For example, the inspection subsystem may be configured to scan a wafer one or more times with different optics modes (assume M modes). The computer subsystem may then be configured for performing commonality analysis to identify which defects were detected in which mode and creating a master list of all unique defects. The computer subsystem may also be configured for creating a multi-mode dataset from the multi-mode inspection by performing the following operation. For each master list defect, collect all features from all modes. Namely, if each mode generates N defect features for every detected defect, a master list defect will have N×M features constructed in the following manner. If a master list defect was detected in mode J, then its features in position [N×(J−1)+1] through [N×J] will include the N features from the mode J. If this master list defect was not detected in mode J, then its features in position [N×(J−1)+1] through [N×J] will be filled with zeroes. The computer subsystem may then perform an adaptive search for defect types as described further herein.

In one such embodiment, searching the other defects includes setting up a defect classification process based on a sample of the other defects, applying the defect classification process to the other defects not included in the sample, and determining a level of confidence of classifications assigned by the defect classification process to the other defects not included in the sample. Searching the other defects may be performed while the wafer is on a SEM review station. The SEM review station may be configured as described above with respect to FIG. 1a (but one or more parameters of the inspection subsystem shown in FIG. 1a may be different depending on whether the electron beam subsystem is to be used for inspection or defect review). In this embodiment, the computer subsystem is configured for sampling a relatively small set of defects from the multi-mode dataset. (This size of the set is subject to characterization, but it would likely be on the order of 5 to 50 defects.) The system may then be configured for SEM review and manually classifying the set of defects. If only one defect type exists in the sample, the computer subsystem may sample another relatively small set of defects. Otherwise, the computer subsystem may be configured for creating a classification model for the known defect types using the training set created by the SEM review and manual classification. The computer subsystem may also be configured for classifying all the remaining defects in the multi-mode inspection results using the classification model created as described above. These defects will be classified into the types known to the model with various levels of confidence.

In some such embodiments, searching the other defects also includes sampling a set of the other defects having the level of confidence that is lower than the level of confidence of others of the other defects, setting up a new defect classification process based on the sample and the sampled set of the other defects, applying the new defect classification process to the other defects not included in the sample and not included in the sampled set of defects, and determining the level of confidence of classifications assigned by the new defect classification process to the other defects not included in the sample or the sampled set of defects. For example, the computer subsystem may be configured for sampling a set of the lowest confidence defects. The lowest confidence defects are defects the model cannot classify well, and they are likely to be new defect types. The size of the sample set is subject to characterization, but it may be on the order of 5 to 50 defects. The system may then be configured for SEM review and manual classification of this set of defects. The computer subsystem may then add these defects to the training set and train a new model. The new model may then be used for classifying all of the remaining defects in the multi-mode inspection results. As with the original model, the defects will be classified into the types known to the model with various levels of confidence. The defects having the lowest levels of confidence may then be sampled, reviewed and manually classified, and then a new model can be generated. These steps can be repeated when the model stops producing relatively tow confidence classifications.

Figure 4:
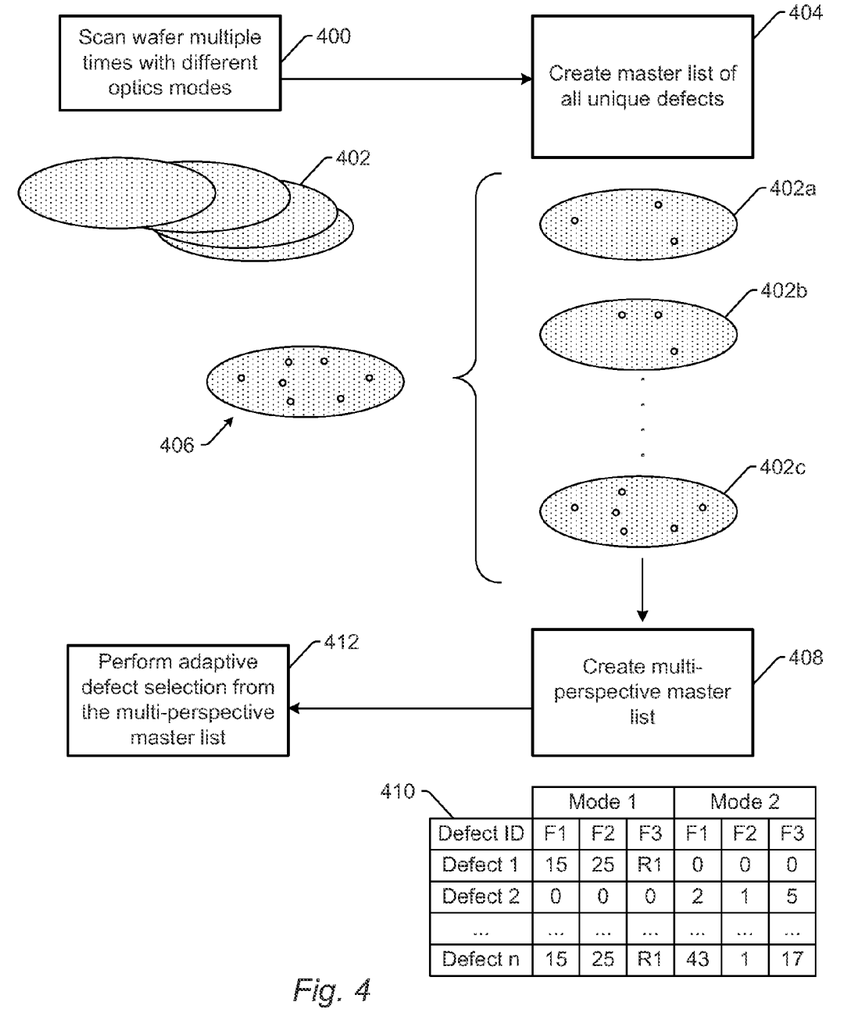
FIGS. 4-5 are flow charts illustrating embodiments of various steps that may be performed by a computer subsystem described herein for discovering defects on a wafer with multiple optical modes of an inspection system.
Figure 5:
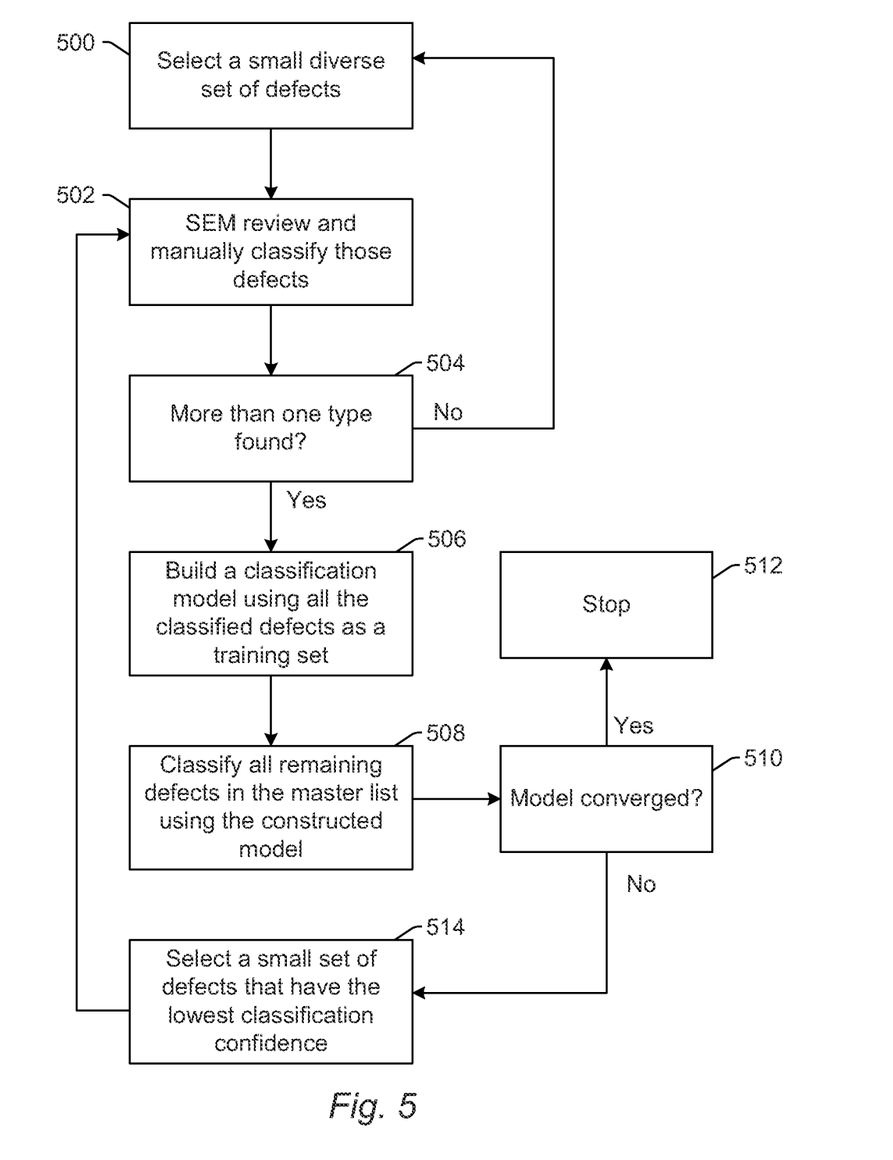

FIGS. 4 and 5 illustrate the defect discovery process for multi-modes. FIG. 4 shows the process for creating the multi-mode master list. FIG. 5 shows the adaptive discovery method, which may be performed on a SEM review station, with the user of the multi-mode information.

As shown in step 400 of FIG. 4, the inspection subsystem may scan a wafer multiple times (one or more times) with different optics modes. The computer subsystem may generate different inspection results 402 for different optics modes. The computer subsystem may then create a master list of all unique defects, as shown in step 404. For example, based on inspection results 402a, 402b, and 402c, the computer subsystem may create master list 406 that includes information for all of the defects detected by all of the modes. If a defect has been detected by more than one mode, the master list may include only one instance of that defect. The computer subsystem may then create a multi-perspective (multi-mode) master list, as shown in step 408. As shown in FIG. 4, the multi-perspective master list may include table 410 or any other suitable data structure in which different defects can be associated with all of the features determined for the defects by all of the modes used to scan the wafer. For instance, in table 410, the ID of the defects may be listed in the first column. Any features determined for the defects may then be listed in additional columns for the defects. For example, as shown in FIG. 4, Mode 1 and Mode 2 may have been used to scan a wafer. Then, values for defect features, F1, F2, and F3, determined for the defects based on output generated using Mode 1 may be listed in columns F1, F2, and F3 under the Mode 1 section of the table. In addition, values for defect features, F1, F2, and F3, determined for the defects based on output generated using Mode 2 may be listed in columns F1, F2, and F3 under the Mode 2 section of the table. In this manner, the features from all modes can be combined into one feature set for each defect. In addition, if a defect was not detected in any of the modes, then the corresponding feature may be designated with zeroes. For example, as shown in table 410, defect 1 was not detected in Mode 2, so the values for features, F1, F2, and F3, in the Mode 2 section of the table are zeros. In another example, as shown in table 410, defect 2 was not detected in Mode 1, so the values for features F1, F2, and F3, in the Mode 1 section of the table are zeros. The computer subsystem may then perform adaptive defect selection from the multi-perspective (multi-mode) master list, as shown in step 412. The adaptive defect selection may be performed as shown in FIG. 5.

As shown in FIG. 5, adaptive discovery, which may be performed on an electron beam defect review tool such as the eDR tools commercially available from KLA-Tencor (while the wafer is on the review tool), may include selecting a small diverse set of defects, as shown in step 500. The adaptive discovery may also include SEM reviewing and manually classifying those defects, as shown in step 502. In addition, the adaptive discovery may include determining if more than one type is found, as shown in step 504. If more than one type has not been found, then the computer subsystem may be configured to repeat the selecting shown in step 500, the reviewing and classifying shown in step 502, and the determining shown in step 504. If more than one type has been found, the computer subsystem may build a classification model using all the classified defects as a training set, as shown in step 506. The computer subsystem may then classify all remaining defects in the master list using the constructed model, as shown in step 508. The computer subsystem determines if the model is converged, as shown in step 510. Convergence is established through monitoring the classification confidence and the stability of the training confusion matrix. The computer subsystem may suggest when to stop, but ultimately a user may decide when to stop based on the suggestion of the computer subsystem. If the model is converged, then the computer subsystem may stop as shown in step 512. If the model is not converged, then the computer subsystem may select a small set of defects that have the lowest classification confidence, as shown in step 514. The computer subsystem may then perform step 500 and other steps described above.

The embodiments described herein have a number of advantages over existing discovery methodology. For example, the embodiments described herein offer a new way of processing multi-mode discovery inspections by combining defect features from multiple modes. Therefore, the embodiments described herein eliminate the need to perform defect discovery independently in each mode and then combine it together. In addition, the multi-mode master list contains information not only about the capture rate of each defect, but also the information about which modes were successful in detecting a defect. This additional information cannot be fully utilized in existing methods used today. The embodiments also provide a mechanism for terminating the discover process and thus avoid the need to develop a BKM for sampling size to be applied to all wafers. This stopping criteria will lead to different SEM review requirements for different wafers. Furthermore, the embodiments described herein can work with all defect features without a loss of effectiveness unlike discovery sampling, which relies on users to select a small set of features to be used for diversification. The embodiments described herein also have the capability to find the defect features that are important in separating defect types, and this suggestion can subsequently be used for a second-round discovery for production recipe tuning. The embodiments described herein can also be combined with other approaches such as diversification, biasing, etc.

Results produced by discovering new defect types using a classification model to select relatively low confidence defects have shown that this approach works just as good as or better than discovery sampling with the additional benefit of being able to suggest the review budget in real time. The characterization also shows that the classification model works sufficiently even with relatively large numbers of defect features (about 500) and even when most of them are noise. This indicates that the multi-mode approach should be extremely valuable. If the discovery is performed on a SEM review station with the wafer on the tool, this discovery could be valuable as a fusion feature with inspection (BBP) and defect review (SEM) working together.

Additional embodiments described herein may be commonly referred to as "1 Test (NanoPoint) NP+process window qualification (PWQ) scans." In general, the embodiments described herein may be used for OSTS for NP. The term "NP" generally refers to a type of inspection that uses extremely small care areas (e.g., on the order of the size of a feature printed on the wafer), whose use is enabled by determining the positions of the "micro care areas" in the output generated by a detector of an inspection system with substantially high accuracy (e.g., on the subpixel level) by, for example, aligning the output of the detector to design data. A PWQ scan generally refers to a type of scan performed by an inspection system on a wafer having formed thereon at least two dies printed on the wafer with different (i.e., modulated) values of one or more parameters of a fabrication process performed on the wafer. Examples of such parameters include, but are not limited to, exposure and dose of a lithography process performed on the wafer.

The embodiments described herein may be used to decrease the setup and run time of NP and PWQ scans on inspection tools such as BBP tools. For example, some currently used methods for PWQ scans using care areas include one test per modulation per mode (with typically about 20 to about 50 modulations), i.e., a separate test for each modulated die, and set sensitivity for each modulation separately using initial threshold finder (ITF), which does a preliminary scan to assess defectivity of the die and then assign a sensitivity based on the percentage assigned by the user, and the time per scan is approximately equal to the full wafer scan time times the number of modulation columns.

The currently used methods have a number of disadvantages. For example, the currently used methods require one test per modulation, which takes much more time on the BBP tool. The time required per scan is that of one full wafer scan multiplied by the number of modulation columns. The extra time required for the scan takes away from the time that could be used for other valuable projects. In addition, the currently used methods require iterative tuning for the ITF percentage. The user starts with the BKM ITF values for each threshold region. Then, the user runs a few modulations and tunes the ITF percentage and repeats the process until the user is satisfied with the ITF percentage.

In contrast, the embodiments described herein may include 1 test per mode, use post-processing to set sensitivity across the wafer, are similar to OSTS except will work for both NP care areas (CAs) and legacy CAs and PWQ as well, and the time per scan is the full wafer scan time. In this manner, the embodiments described herein have a number of advantages over currently used methods such as better ease of use and decreased scan time on the inspection tool, e.g., BBP tool, which can be used for other projects. For example, inspection tools' such as BBP tools time is extremely valuable as any extra tool time can be used to do production scans or other recipe setup. In addition, the enhanced ease of use will make recipe setup time faster. This time savings is crucial for inspection tool users and can save them millions of dollars.

In one embodiment, the inspection subsystem is configured to scan the energy over another wafer while the detector generates the output, the other wafer is a PWQ wafer on which at least two dies are printed with different values for one or more parameters of a process used to print the wafer, and the computer subsystem is configured for identifying micro care areas in the output and detecting other defects based on the output in the micro care areas. For example, the embodiments may be utilized in any NP+PWQ flow for the BBP scans. The embodiments can also be used in regular NP scans in place of a hot scan for easier segment and threshold tuning. The inspection subsystem may be configured to scan the energy over the wafer as described further herein. The computer subsystem may be configured to identify the micro care areas in the output as described further herein (e.g., by aligning the output of the detector to design data for the wafer). The computer subsystem may also be configured to detect defects based on the output in the micro care areas in any suitable manner, e.g., by applying a defect detection algorithm and/or method to only the output generated in the micro care areas.

In this manner, the embodiments described herein may use one test for all modulations instead of one test for each separate modulation. Instead of using ITF, the embodiments described herein may use a new algorithm that would provide one-step tuning. This new algorithm named OSTS for NP would be similar to OSTS except that it would work on NP and legacy care areas (CAs) instead of just legacy CA. The embodiments improve on the old method as they greatly reduce both setup and run time. During setup, the user would just need to specify the defect limit and choose the new algorithm. There would be no need for further iterations. During runtime, the scan time would take as long as the full wafer scan, which is multiple times faster than the scan time using the old method.

In one such embodiment, the scan is performed for two or more of the at least two dies printed with different values and one or more modes of the inspection subsystem, detecting the other defects includes generating one or more defect populations for the one or more modes, respectively, and each of the one or more defect populations includes the other defects detected in the two or more of the at least two dies. In this manner, each scan may be performed for at least two modulated dies and one or more modes of the inspection subsystem. A defect population generated by any one scan may, therefore, include defects in the at least two modulated dies that are scanned in that one scan. In some such embodiments, the one or more defect populations for the one or more modes, respectively, include approximately the same number of defects for each of the two or more of the at least two dies. For example, the new algorithm, OSTS for NP, may run a scan of a certain percentage across the wafer to assess the defectivity. Using this information, the algorithm may allocate defects across the wafer such that the defects would be evenly distributed across the dies, ensuring that there are similar defect counts for all modulations.

In additional such embodiments, the computer subsystem is configured for selecting one or more parameters for inspection of additional PWQ wafers with at least one of the one or more modes based on the one or more defect populations for the one or more modes, respectively. For example, the algorithm allows for one-step tuning for PWQ and evenly distributes defects across modulations. Due to one-step tuning, the user would no longer have to iteratively tune thresholds. This would also reduce the number of tests from one per modulation to one for all modulations, greatly reducing the scan time. Selecting the parameters for inspection of the additional PWQ wafers may be performed in any suitable manner.

A variation on the embodiments described above may include trying to group sets of similar modulations to decrease the number of tests and possibly the scan time. However, this would mean running hot scans for multiple modulations to check which modulations could be grouped. In addition, this would still lead to several tests and a scan time that is longer than that of the embodiments described herein.

Another embodiment relates to a computer-implemented method for discovering defects on a wafer. The method includes detecting defects on a wafer by applying a threshold to output generated by a detector of an inspection system in a first scan of the wafer. The inspection system may be configured as described herein with respect to an inspection subsystem. The method also includes steps for determining the values, automatically ranking the features, identifying the features, determining one or more parameters, and applying the one or more determined parameters described herein. These steps are performed with a computer system, which may be configured as described further herein.

The method described above may include step(s) for performing any other one or more function(s) of the system embodiment(s) described herein. Furthermore, the method described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 6:
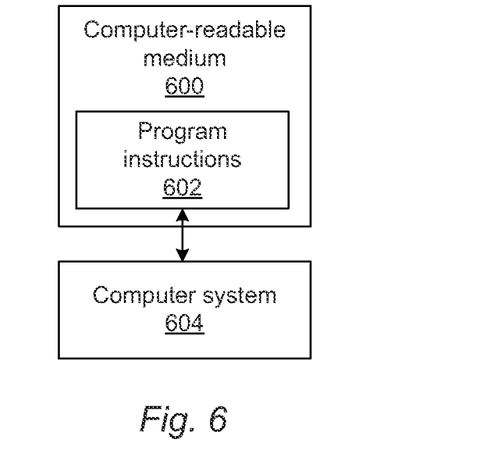
FIG. 6 is a block diagram illustrating one embodiment of a non-transitory computer-readable medium storing program instructions for causing a computer system to perform a computer-implemented method described herein.

Another embodiment relates to a non-transitory computer-readable medium storing program instructions executable on a computer system for performing a computer-implemented method for discovering defects on a wafer. One such embodiment is shown in FIG. 6. For example, as shown in FIG. 6, non-transitory computer-readable medium 600 stores program instructions 602 executable on computer system 604 for performing a computer-implemented method for discovering defects on a wafer. The computer-implemented method may include any step(s) of any method(s) described herein.

Program instructions 602 implementing methods such as those described herein may be stored on non-transitory computer-readable medium 600. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 604 may be further configured as described herein.

Further modifications and alternative embodiments of various aspects of the invention will be apparent to those skilled in the art in view of this description. For example, systems and methods for discovering defects on a wafer are provided. Accordingly, this description is to be construed as illustrative only and for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to discover defects on a wafer, comprising:
    an inspection subsystem comprising at least an energy source and a detector, wherein the energy source is configured to generate energy that is directed to and scanned over a wafer, and wherein the detector is configured to detect energy from the water and to generate output responsive to the detected energy; and
    a computer subsystem configured for:
        detecting defects on the wafer by applying a threshold to the output generated by the detector in a first scan of the wafer;
        determining values for features of the detected defects;
        based on the values for the features, automatically ranking the features and identifying feature cut-lines to group the defects into bins;
        for each of the bins, determining one or more parameters that if applied to the values for the features of the defects in said each of the bins will result in a predetermined number of the defects in said each of the bins; and
        applying the one or more determined parameters to the output generated by the detector in a second scan of the wafer to generate a defect population, wherein the defect population has a predetermined defect count and is diversified in the values for the features.

2. The system of claim 1, wherein the computer subsystem is further configured for performing said detecting, said determining the values, said automatically ranking, said identifying, said determining the one or more parameters, and said applying automatically and without manual recipe setup.

3. The system of claim 1, wherein the one or more determined parameters comprise one or more thresholds.

4. The system of claim 1, wherein the threshold is at a noise floor of the output.

5. The system of claim 1, wherein the threshold is automatically selected by the computer subsystem.

6. The system of claim 1, wherein the predetermined number of the defects is selected by a user.

7. The system of claim 1, wherein the predetermined number of the defects is different for at least two of the bins.

8. The system of claim 1, wherein the one or more determined parameters comprise one or more parameters for nuisance filtering.

9. The system of claim 1, wherein the inspection subsystem is configured to scan the wafer with different modes.

10. The system of claim 9, wherein the computer subsystem is further configured for detecting other defects based on the output generated with the different modes, determining values for features of the other defects using the output generated with the different modes, and performing defect discovery based on a combination of all of the values for all of the features determined for all of the defects.

11. The system of claim 9, wherein the computer subsystem is further configured for detecting other defects based on the output generated with the different modes, comparing the other defects to identify the different modes with which each of the other defects was detected, determining a set of features for each of the other defects, wherein the set of features is determined based on the output generated with the different modes, and searching the other defects for different types of defects based on the set of features.

12. The system of claim 11, wherein said searching comprises setting up a defect classification process based on a sample of the other defects, applying the defect classification process to the other defects not included in the sample, and determining a level of confidence of classifications assigned by the defect classification process to the other defects not included in the sample.

13. The system of claim 12, wherein said searching further comprises sampling a set of the other defects having the level of confidence that is lower than the level of confidence of others of the other defects, setting up a new defect classification process based on the sample and the sampled set of the other defects, applying the new defect classification process to the other defects not included in the sample and not included in the sampled set of defects, and determining the level of confidence of classifications assigned by the new defect classification process to the other defects not included in the sample or the sampled set of defects.

14. The system of claim 1, wherein the inspection subsystem is configured to scan the energy over another wafer while the detector generates the output, wherein the other wafer is a process window qualification wafer on which at least two dies are printed with different values for one or more parameters of a process used to print the wafer, and wherein the computer subsystem is further configured for identifying micro care areas in the output and detecting other defects based on the output in the micro care areas.

15. The system of claim 14, wherein the scan is performed for two or more of the at least two dies printed with the different values and one or more modes of the inspection subsystem, wherein detecting the other defects comprises generating one or more defect populations for the one or more modes, respectively, and wherein each of the one or more defect populations comprises the other defects detected in the two or more of the at least two dies.

16. The system of claim 15, wherein the one or more defect populations for the one or more modes, respectively, comprise approximately the same number of defects for each of the two or more of the at least two dies.

17. The system of claim 15, wherein the computer subsystem is further configured for selecting one or more parameters for inspection of additional process window qualification wafers with at least one of the one or more modes based on the one or more defect populations for the one or more modes, respectively.

18. The system of claim 1, wherein the energy source is a broadband plasma light source.

19. A computer-implemented method for discovering defects on a wafer, comprising:
    detecting defects on a wafer by applying a threshold to output generated by a detector of an inspection system in a first scan of the wafer, wherein the inspection system comprises at least an energy source and the detector, wherein the energy source is configured to generate energy that is directed to and scanned over the wafer, and wherein the detector is configured to detect energy from the wafer and to generate the output responsive to the detected energy;
    determining values for features of the detected defects;
    based on the values for the features, automatically ranking the features and identifying feature cut-lines to group the defects into bins;
    for each of the bins, determining one or more parameters that if applied to the values for the features of the defects in said each of the bins will result in a predetermined number of the defects in said each of the bins; and
    applying the one or more determined parameters to the output generated by the detector in a second scan of the wafer to generate a defect population, wherein the defect population has a predetermined defect count and is diversified in the values for the features, and wherein said detecting, said determining the values, said automatically ranking, said identifying, said determining the one or more parameters, and said applying are performed with a computer system.

20. A non-transitory computer-readable medium, storing program instructions executable on a computer system for performing a computer-implemented method for discovering defects on a wafer, wherein the computer-implemented method comprises:
    detecting defects on a wafer by applying a threshold to output generated by a detector of an inspection system in a first scan of the wafer, wherein the inspection system comprises at least an energy source and the detector, wherein the energy source is configured to generate energy that is directed to and scanned over the wafer, and wherein the detector is configured to detect energy from the wafer and to generate the output responsive to the detected energy;
    determining values for features of the detected defects;
    based on the values for the features, automatically ranking the features and identifying feature cut-lines to group the defects into bins;
    for each of the bins, determining one or more parameters that if applied to the values for the features of the defects in said each of the bins will result in a predetermined number of the defects in said each of the bins; and
    applying the one or more determined parameters to the output generated by the detector in a second scan of the wafer to generate a defect population, wherein the defect population has a predetermined defect count and is diversified in the values for the features.

* * * * *

UNITED STATES PATENT AND TRADEMARK OFFICE
CERTIFICATE OF CORRECTION

PATENT NO. : 9,518,934 B2  
APPLICATION NO. : 14/931226  
DATED : December 13, 2016  
INVENTOR(S) : Hong Chen et al.

Page 1 of 1

It is certified that error appears in the above-identified patent and that said Letters Patent is hereby corrected as shown below:

In the Claims

Column 19
Line 51, please delete "water" and insert --wafer--.

Signed and Sealed this
Second Day of January, 2018

Joseph Matal
*Performing the Functions and Duties of the*
*Under Secretary of Commerce for Intellectual Property and*
*Director of the United States Patent and Trademark Office*